United States Patent
Spencer, II

(10) Patent No.: US 8,531,090 B2
(45) Date of Patent: Sep. 10, 2013

(54) CRYSTAL MICROBALANCE HOLDER

(75) Inventor: Joseph Allen Spencer, II, Longmont, CO (US)

(73) Assignee: ALD Nanosolutions Inc., Boulder, CO (US)

( * ) Notice: Subject to any disclaimer, the term of this patent is extended or adjusted under 35 U.S.C. 154(b) by 237 days.

(21) Appl. No.: 13/181,713

(22) Filed: Jul. 13, 2011

(65) Prior Publication Data
US 2011/0266924 A1 Nov. 3, 2011

(51) Int. Cl.
*H01L 41/053* (2006.01)

(52) U.S. Cl.
USPC ............................................. 310/348

(58) Field of Classification Search
USPC ................................. 310/344, 348
See application file for complete search history.

(56) References Cited

U.S. PATENT DOCUMENTS

| | | | | |
|---|---|---|---|---|
| 5,306,981 A * | 4/1994 | Martel et al. | ................... | 310/348 |
| 6,033,852 A * | 3/2000 | Andle et al. | .................. | 435/6.11 |
| 6,268,683 B1 * | 7/2001 | Li | ................... | 310/348 |
| 7,275,436 B2 * | 10/2007 | Grimshaw | ...................... | 73/579 |
| 2006/0082259 A1 * | 4/2006 | Schlenke | ...................... | 310/348 |

OTHER PUBLICATIONS

Inficon(TM) Bakable Crystal Sensor Operating Manual, 2003.
Elam et al., "Viscous flow reactor with quartz crystal microbalance for thin film growth by atomic layer deposition", Review of Scientific Instruments 73(8), 2002, pp. 2981-2987.

* cited by examiner

*Primary Examiner* — Thomas Dougherty
(74) *Attorney, Agent, or Firm* — Gary C Cohn PLLC

(57) ABSTRACT

A piezoelectric element holder allows a piezoelectric crystal to be mounted with a single exposed surface. This permits more accurate estimates of applied coating weights and thicknesses to be obtained. The piezoelectric element is mounted via a removable cap and malleable seal that permit the element to be removed and replaced easily.

8 Claims, 3 Drawing Sheets

CRYSTAL MICROBALANCE HOLDER

This invention relates to a crystal microbalance holder.

Crystal microbalances are used to weigh very small masses. They are commonly employed to monitor coating processes such as sputtering and chemical vapor deposition. The working element of a crystal microbalance is a piezoelectric element, which is typically a piezoelectric crystal. Under an applied oscillating current, the crystal will vibrate or oscillate in phase with the voltage. Each crystal has a natural resonance frequency at which the crystal vibrates with minimal resistance. This frequency varies with mass, and changes in the resonance frequency therefore are indicative of changes in mass of the crystal. In a coating process, the microbalance is present in the coating chamber in which a coating is applied to some substrate. The crystal becomes coated at the same time as the substrate. Presumably, the rate of growth of the coating on the crystal is the same or nearly the same as that on the substrate. By measuring the changes in resonance frequency in the crystal, the mass of the applied coating and therefore its thickness can be estimated, both for the crystal itself and the substrate. These microbalances often provide accurate estimates of coating thicknesses of as little as a few nanometers.

Most coating processes that are used to apply very thin coatings such as these are so-called "line-of-sight" methods. That is, the coating material must transverse some space in a specific direction from a source to the "target", i.e., the substrate that is to be coated. The coating material therefore only contacts those surfaces of the substrate that face the source. Surfaces that are obscured do not become coated.

Likewise, a crystal microbalance used in a line-of-sight coating process will be coated only on that portion of the surface that directly faces the source of the coating material. Other surfaces of the crystal remain uncoated in these processes. Because of this, the area of the crystal that becomes coated is controlled directly through the size of the crystal and its orientation relative to the source. Line-of-sight coating processes also avoid deposition in components of the crystal microbalance that make electrical connections.

Some processes, like atomic layer deposition, are not line-of-sight processes. In atomic layer deposition, the reactants that form the coating are gaseous; therefore, they will fill the entire chamber and deposit onto any exposed surface of the crystal. This makes it more difficult to correlate the mass of the deposited coating to its thickness, as the surface area of the crystal that becomes coated often is not known with precision. In addition, "dead spots" can form behind the crystal in an ALD process. These dead spots can be more difficult to purge between the sequential introductions of the ALD reagents. Because of this, the reagents can react in the gas phase rather than at the crystal surface in these dead spots and deposit as a chemical vapor deposition coating rather than as an ALD coating. The thickness of such a chemical vapor deposition coating is often quite different than that of the ALD-deposited film and as a result the measured weight of the coating does not accurately correlate to the thickness of the ALD coating. Conducting or semiconducting ALD coatings can bridge the electrically separated surfaces of the piezoelectric element, shorting the circuit.

Because of these problems, the crystal holders used in the line of sight coating methods are not designed suitably for use in atomic layer deposition methods, or other methods that are not line-of-sight. When used in atomic layer deposition processes, those crystal holders permit the gaseous reactants to deposit onto any exposed surface of the crystal, including surfaces that do not face the source of the reactants. Therefore, the amount of surface area that is coated becomes less predictable and coating thickness cannot easily be calculated from the measured coating weight. In addition, the thickness of the coating that is applied to the crystal may not be uniform due to chemical vapor deposition reactions that can occur in dead spots, and so the measured mass increases may not accurately reflect the thickness of the coating applied to the substrate. Conventional crystal holders do not solve the problem of applied conductive coatings short-circuiting the element.

Attempts have been made to adapt the crystal holders to atomic layer deposition methods. The general idea is to isolate all crystal surfaces except the front side (that facing the reagent source) from the reagents, so the coating forms only onto a defined area of the crystal surface. These modified crystal holders have been so adapted by using a conductive epoxy resin to seal the top side of the crystal to a sample holder. This method is tedious because multiple epoxy curing steps are needed. In addition, the embedded crystal is very difficult to remove and replace.

A need exists for a crystal holder that can isolate all but the front surface of the crystal, while still being easy to remove and replace. The design should be capable of withstanding temperatures of 500° C. or more that are often encountered in ALD processes and to be compatible with common crystal types such as quartz, langasite and $GaPO_4$ crystals.

This invention is a holder for a piezoelectric element having an exposed side and an reverse side, comprising:

A. a body;
B. a piezoelectric element support mounted on or forming a part of the body;
C. a first electrode;
D. a removable cap mounted on the body;
E. a malleable seal;
F. and electrical circuit means for connecting the first electrode and the piezoelectric element to an oscillating current source such that when connected to such an oscillating current source an applied oscillating current flows through an electrical circuit that includes the first electrode and the piezoelectric element, wherein the body, piezoelectric element support, first electrode, removable cap and malleable seal are adapted such that, when a piezoelectric element is mounted in the holder:

1. the piezoelectric element support holds the piezoelectric element and together with the piezoelectric element defines an enclosed region on a reverse side of the piezoelectric element;
2. the first electrode is in electrical contact with at least one point of one side of the piezoelectric element;
3. an exposed side of the piezoelectric element, opposite of said reverse side, is exposed through openings in the malleable conductive seal and the removable cap;
4. the malleable seal (a) is located between the removable cap and the piezoelectric element, (b) holds the piezoelectric element or piezoelectric element support/piezoelectric element assembly in place within the holder and (c) forms a seal around the piezoelectric element or around the piezoelectric element support that prevents gasses from entering from the exposed side of the piezoelectric element into the enclosed region defined by the piezoelectric element support and the piezoelectric element; and
5. the electrical circuit means includes at least one point of contact spaced apart from the point of contact of the first electrode with the piezoelectric element.

This holder presents a defined surface of the piezoelectric element to the coating chamber, and permits the piezoelectric element to be installed, removed and replaced easily and rapidly. Surprisingly, measurements made using this apparatus are unexpectedly accurate, precise and reproducible.

Figure 1:
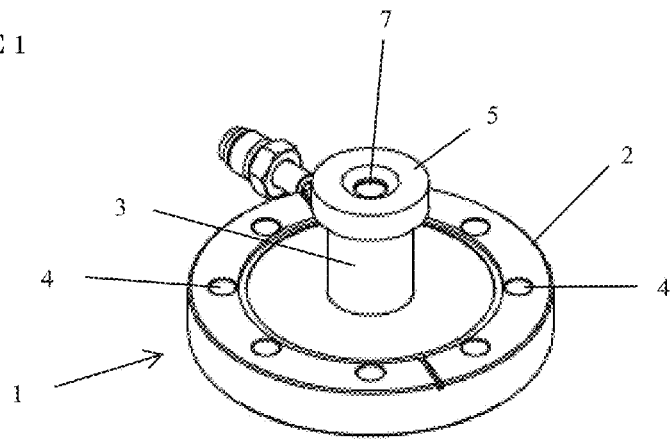
FIG. 1 is a top isometric view of a piezoelectric element holder of the invention.
Figure 2:
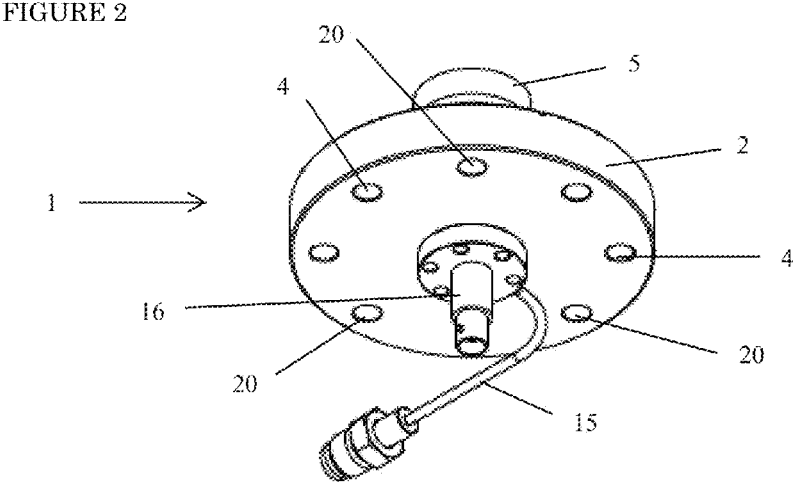
FIG. 2 is a bottom isometric view of a piezoelectric element holder of the invention.

Turning to FIGS. 1 and 2, piezoelectric element holder 1 includes body 3 and cap 5. Cap 5 and malleable seal 10 together define opening 7 through which a piezoelectric element held within holder 1 is exposed. By "exposed", it is meant that, exposed side 22 of piezoelectric element 7 is in fluid communication with the surrounding atmosphere, such that gasses in the surrounding atmosphere can make contact with exposed side 22. Opening 7 may be uncovered or may be partially covered. Opening 7 defines the surface area of piezoelectric element 8 that is exposed and which is available for coating during a deposition process.

The embodiment shown in FIGS. 1 and 2 includes optional flange 2 through which piezoelectric element holder 1 is mounted onto a wall of a vapor deposition apparatus (not shown). Holes 4 are provided to allow flange 2 to be mounted to the vapor deposition apparatus via bolts (not shown) or similar means. In the embodiment shown, seal 17 provides a gas-tight seal when piezoelectric element holder 1 is mounted on the vapor deposition apparatus. Other means of affixing piezoelectric element holder 1 to the vapor deposition apparatus can be substituted for the particular arrangement shown in FIGS. 1 and 2.

Body 3 may be affixed to flange 2 in any convenient manner. Body 3 may be, if desired, permanently affixed to flange 2 by, for example, welding, riveting, gluing or other means. Alternatively, body 3 may be removably affixed to flange 2 using various affixing means such as reciprocal threading in body 3 and flange 2, screws or bolts, clips, or other removable fastening means.

Body 3 is elongated sufficiently that, when mounted on a deposition chamber, piezoelectric element 8 becomes situated within the deposition chamber. The geometry of body 3 may be adjusted in any particular case to orient piezoelectric element 8 in a desirable sampling location within the chamber.

Figure 3:
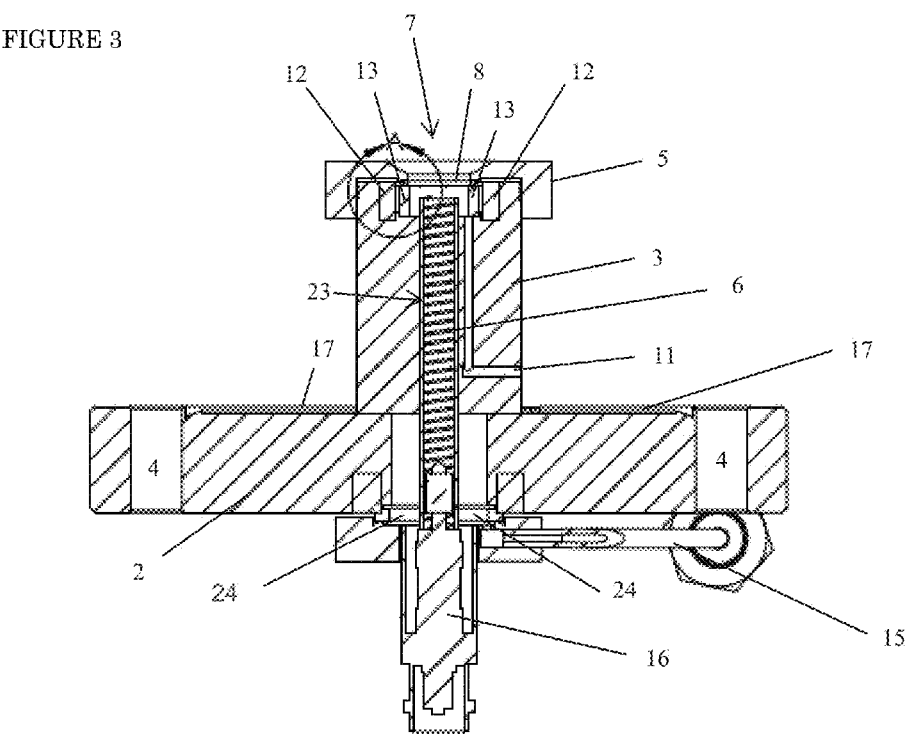
FIG. 3 is a cross-sectional view of a piezoelectric element holder of the invention.
Figure 3A:
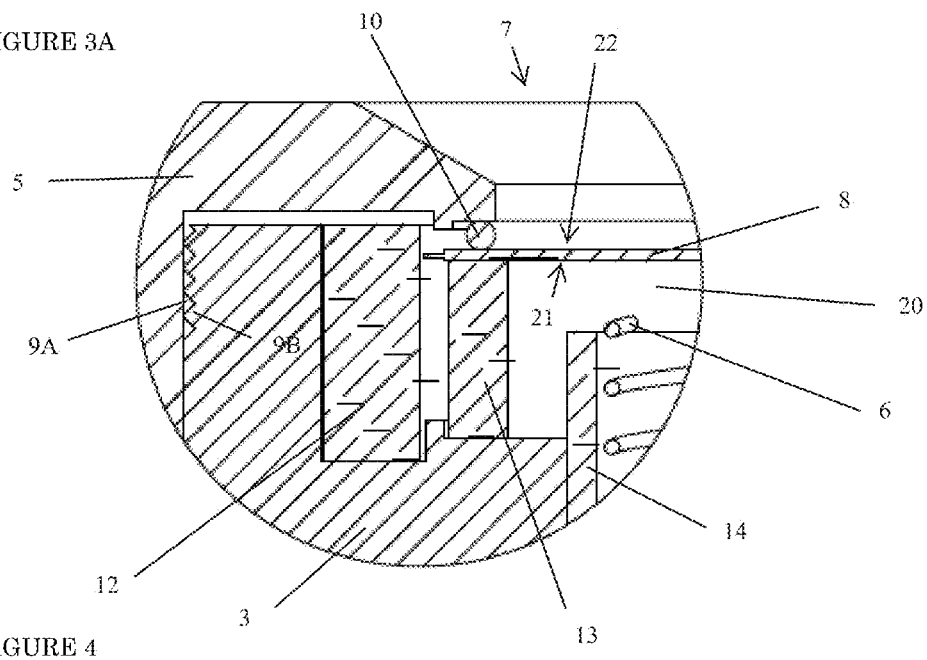
FIG. 3A is an enlarged detail, in cross-section, of a portion of the piezoelectric element holder of the invention.

As shown in FIGS. 3 and 3A, body 3 forms a housing upon which the other elements of the holder are mounted. In the embodiment shown, piezoelectric element support 13 is mounted onto body 3. Piezoelectric element support 13 holds piezoelectric element 8, preferably but not necessarily about its periphery. The center of piezoelectric element 13 preferably is unsupported or at most lightly supported, so that piezoelectric element 13 can vibrate when an oscillating current is applied during operation. Support 13 and piezoelectric element 8 together define enclosed region 20 on reverse side 21 of piezoelectric element 8.

In the embodiment shown, piezoelectric element 8 merely rests against support 13 without being affixed thereto, and is held into place against support 13 via removable cap 5 and malleable seal 10. Malleable seal 10 is positioned between removable cap 5 and piezoelectric element 8, and forms a seal around piezoelectric element 13 that prevents gasses from entering into enclosed region 20 from the exposed side 21 of piezoelectric element 8. In an alternative embodiment, support 13 may mechanically grip the periphery of piezoelectric element 8, and hold it in place within body 3 without the assistance of malleable seal 10 and removable cap 5; in such embodiments, malleable seal 10 performs the sealing function just described although it does not necessarily mechanically hold piezoelectric element 8 in place. Piezoelectric element 8 should not be glued or otherwise adhered to support 8, as doing so makes it difficult to remove and replace piezoelectric element 8.

In the embodiment shown, electrode 6 is in electrical contact with at least one point on reverse side 21 of piezoelectric element 8. It is possible to arrange the features so that electrode 6 is in electrical contact with exposed side 22 of piezoelectric element 8.

Electrode 6 should make only light contact with piezoelectric element 8, so as not to significantly constrain its vibration under an applied oscillating current. Electrode 8 is preferably spring-mounted. In the embodiment shown in FIGS. 3 and 3A, electrode 6 itself takes a form of a simple coiled spring, which is situated within a central bore in body 3. A useful alternate design for a spring-mounted electrode is described in U.S. Pat. No. 7,275,436. In an especially simple design, electrode 6 is simply a flexible wire or conductive material.

Figure 4:
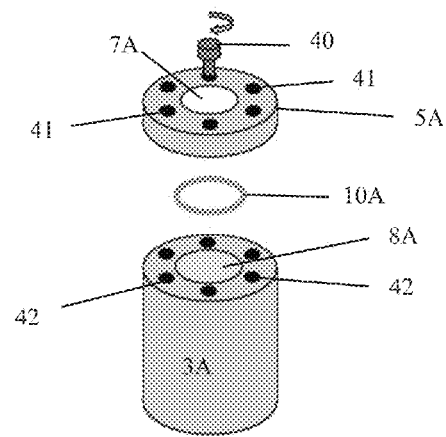
FIG. 4 is a top isometric view of another embodiment of the piezoelectric element holder of the invention.

Cap 5 is removably mounted onto body 3. By "removably mounted", it is meant that cap 5 is mechanically mounted onto body 3 in a manner that allows it to be repeatedly removed and replaced, without the use of an adhesive or other sealing material that must be broken to remove cap 5 from body 3. In the embodiment shown in FIGS. 3 and 3A, both cap 5 and body 3 are threaded (as indicated by reference numerals 9A and 9B, respectively). Cap 5 is screwed onto body 3 and removed from body 3 by unscrewing it. This design allows cap 5 to be applied to a prespecified torque. The tolerance between cap 5 and body 3 can also be controlled such that when screwed into place, the surfaces of cap 5 and body 3 meet preventing further compression of malleable seal 10 beyond what is desired. An alternative design is shown in FIG. 4. In FIG. 4, cap 5A is a halo design (ring) that includes opening 7A and bore holes 41. In the embodiment shown in FIG. 4, body 3A includes threaded holes 42 through which cap 5A is fastened to body 3A via bolts such as bolt 40. Malleable conductive seal 10A is interposed between cap 5A and piezoelectric element 8A as elsewhere described. Alternatively, various types of clips and other mechanical fastening means can be provided to removably affix cap 5 to body 3. Cap 5 can be snap-fitted onto body 3. Cap 5 may includes various design features such as holes and/or planar edge surfaces that allow it to be gripped and/or manipulated with a specialized tool or torque wrench to be adjusted to a particular tightness.

The electrical circuit means for connecting the first electrode and the piezoelectric element to an oscillating current source is simply an electrical path through which electrical current can flow from one electrode of the oscillating current source, through the first electrode 6, through the piezoelectric element and then to the other electrode of the current source, thus completing the electrical circuit. Thus, the electrical circuit means includes a first electrical contact through which current can be supplied to electrode 6, and an electrical pathway from piezoelectric element 8 to a second electrical contact for connection to the second electrode of the oscillating current source. The electrical circuit means includes at least one point of contact the piezoelectric element that is spaced apart from the point of contact of electrode 6 with piezoelectric element 8. Thus, in the embodiment shown, electrode 6 is in contact with reverse side 21 of piezoelectric element 8, and therefore the electrical circuit means includes another point of contact with piezoelectric element 8, and which is spaced apart from electrode 6. This point of contact is spaced far enough apart from the point(s) of contact of the first electrode of the piezoelectric element so that arcing does not occur during operation. Other elements of the holder typically form all or part of this electrical pathway from the piezoelectric element 8 to the second electrical contact that is connected to the second electrode of the oscillating current source.

In the embodiment shown in FIG. 3, body 3, cap 5 and malleable seal 10 form part this electrical pathway current from piezoelectric element 8 to the second electrical contact for connection with the oscillating current source. In such embodiments, body 3, cap 5 and malleable seal 10 are all made of an electrically conductive material. Body 3 is in electrical contact with cap 5 and cap 5 is in electrical contact with malleable conductive seal 10. In the embodiment shown in FIG. 3, flange 2 forms still another portion of this electrical pathway, conducting current between body 3 and an electrical contact situated on plug 16.

In the embodiment shown, electrode 6 also is electrically connected to an electrical contact situated on plug 16. Plug 16 is conveniently a male or female receptacle is adapted to fix into or receive a reciprocating receptacle that connects the electrical contacts of plug 16 to the electrodes of an oscillating current source. Plug 16 may be a vacuum compatible insulating feed through. Plug 16 can be part of a unitary structure that includes flange 2. As shown, plug 16 is separately made, and affixed to flange 2 via screws and/or bolts that pass through holes 20 (FIG. 2). A gasket 24 (FIG. 3) may be interposed between plug 16 and flange 2 to provide a vacuum seal.

In an embodiment such as is shown in FIGS. 3 and 3A, support 13 is made of an insulating material, so that current cannot flow from piezoelectric element 8 directly to body 3, but instead flows through malleable seal 10 and then through cap 5. In such an embodiment, it is necessary to prevent electrode 6 from coming in direct electrical contact with body 3. In the embodiment shown, insulating sleeve 14 separates electrode 6 from body 3. Insulating sleeve 14 is made of an electrically insulating material.

Ceramic insulator 12 provides further electrical insulation between piezoelectric element 8 and body 3, again to prevent short-circuiting.

During operation, an oscillating current is applied across piezoelectric element 8 via malleable seal 10 and electrode 6. Therefore, malleable seal 10 and electrode 6 each are in electrical contact with piezoelectric element 8 (but not directly with each other, to avoid short-circuiting). The current supplied via malleable seal 10 and electrode 6 therefore flows through piezoelectric element 8. The resonance of piezoelectric element 8 in response to the applied oscillating current is indicative of its mass and the mass of an applied coating. Because the exposed surface area of piezoelectric element 8 is defined by opening 7 and is therefore known, the measured mass of the applied coating can be correlated directly to a coating thickness.

In an alternative embodiment, malleable seal 10 is electrically insulating and support 13 is electrically conductive. In such an alternative embodiment, the current flows through electrode 6, through piezoelectric element 8 and through support 13 and body 3. As before, the resonance of piezoelectric element 8 in response to the applied oscillating current is correlated to a coating thickness.

It is also possible that body 3 is not conducting. In such a case, a separate electrical path is provided from piezoelectric element 8 to plug 16 to complete the electrical circuit means.

The embodiment shown in FIGS. 1-3 includes various optional features. Vent 11 places enclosed region 20 into fluid communication with the exterior of body 3. This allows the pressure in enclosed region 20 to be equilibrated to that on exposed side 22 of piezoelectric element 8, and also permits a purge gas to be introduced and removed as may be desired.

Optional tube 15 is in fluid connection with a source of a purge gas and with enclosed region 20. Typically, tube 15 will be in fluid communication with bore 23 in body 3 (which also holds electrode 6), and permits a purge gas to be delivered to enclosed region 20 through bore 23. The purge gas then escapes through vent 11. Vent 11 is typically in fluid communication with the interior of the deposition chamber during operation, and the purge gas is vented into the deposition chamber. Tube 15 may include valving means for controlling the rate of flow of the purge gas during operation. Alternatively, tube 15 may be in fluid communication with a separate mass flow controller which controls the rate of purge gas feed into tube 15.

Heating means for heating or otherwise controlling the temperature of piezoelectric element 8 also may be included as part of the holder. A suitable design and manner of operation of such heating means is described, for example, in U.S. Pat. No. 7,275,436, incorporated herein by reference. In another design, a heater element may be in contact with the exterior of body 3 and/or the exterior of flange 2, to provide temperature control to piezoelectric element 8 and surrounding apparatus.

Malleable seal 10 is made of a soft material that deforms easily under an applied pressure to form a seal. The material must be capable of withstanding the operating temperatures encountered in the deposition process without melting, subliming or degrading such that the seal is lost. When malleable seal 10 forms all or part of the second electrode that is in contact with piezoelectric element 8, or otherwise part of the electrical circuit, it is also electrically conducting. Preferred materials of construction for malleable seal 10 include soft metals. Gold and gold alloys that contain 50% or more by weight gold are especially preferred. Deformable organic polymers that contain conductive fillers also can be used to make a conductive malleable seal.

Piezoelectric element 8 can be any material that exhibits a reversible dimensional change under an applied oscillating electrical current. Preferred piezoelectric element materials include various crystals such as quartz, langasite and gallium phosphate. Quartz crystals include, for example, AT-cut, SC-cut, IT-cut or near-IT-cut crystals, including crystals as described in U.S. Pat. No. 7,275,436.

Support 13 is made of an electrically conductive material in cases in which it forms part of the electrical circuit, or otherwise of an electrical resistor. The remaining components of the holder of the invention are conveniently made from materials that possess the needed mechanical and electrical characteristics required for their respective functions. Components that form part of the electrical circuit of course must be made of electrically conductive materials.

Other optional features include a thermocouple well penetrating body 3 into enclosed region 20, fitted with a thermocouple which during operation monitors the temperature in enclosed region 20 proximate to piezoelectric element 8.

It is possible to mount two or more bodies 2 onto a single flange 3, or to adapt a single body 2 to hold two or more piezoelectric elements in the manner described herein.

The holder of the invention with mounted piezoelectric element is conveniently used in the same manner as previous piezoelectric holders. No special operating conditions are needed. The holder is mounted onto or inside of a deposition chamber such that the exposed surface of the piezoelectric element is expose, during operation, to the deposition material. Coating weights are measured by applying an oscillating current across the piezoelectric element via the first electrode and the electrical circuit, and measuring its vibration and/or resonance in response to frequency of the applied oscillating current.

The holder/piezoelectric element assembly is useful for measuring the weights of coatings that are applied in a wide range of deposition processes, but is especially useful in non-line-of-sight processes, such as atomic layer deposition processes. In an atomic layer deposition process, two or more gas phase reactants are separately and alternatingly introduced into the deposition chamber, where they contact the surface of the substrate and the exposed surface of the piezoelectric element. The reactants are not capable of reacting with themselves under the conditions of the process. Each reactant reacts at the surface of the substrate and the piezoelectric, each in turn forming a mono-layer of deposited material. Excess amounts of reactant are removed from the reaction zone before introducing the next reactant. Reaction by-products are removed as well, between successive introductions of the reagents. This procedure ensures that reactions occur at the surface of the substrate, rather than in the gas phase.

A purge gas is typically introduced between the alternating feeds of the reactants, in order to further help to remove excess reactants. A carrier gas, which is usually but not necessarily the same as the purge gas, generally (but not always necessarily) is introduced during the time each reactant is introduced.

Reaction conditions are selected mainly to meet two criteria. The first criterion is that the reagents are gaseous under the conditions of the reaction. Therefore, temperature and pressure conditions are selected such that the reactants are volatilized. The second criterion is one of reactivity. Conditions, particularly temperature, are selected such that the desired reaction between the film-forming reagents (or, at the start of the reaction, the first-introduced reagent and the particle surface) occurs at a commercially reasonable rate.

The temperature of the reactions may range from 250-1000K. Subatmospheric pressures will normally be required, but some processes can be performed at atmospheric or higher pressures.

What is claimed is:

1. A holder for a piezoelectric element having an exposed side and an reverse side, comprising:
   A. a body;
   B. a piezoelectric element support mounted on or forming a part of the body;
   C. a first electrode;
   D. a removable cap mounted on the body;
   E. a malleable seal;
   F. and electrical circuit means for connecting the first electrode and the piezoelectric element to an oscillating current source such that when connected to such an oscillating current source an applied oscillating current flows through an electrical circuit that includes the first electrode and the piezoelectric element,
   wherein the body, piezoelectric element support, first electrode, removable cap and malleable seal are adapted such that, when a piezoelectric element is mounted in the holder:
   1. the piezoelectric element support holds the piezoelectric element and together with the piezoelectric element defines an enclosed region on a reverse side of the piezoelectric element;
   2. the first electrode is in electrical contact with at least one point of one side of the piezoelectric element;
   3. an exposed side of the piezoelectric element, opposite of the reverse side, is exposed through openings in the malleable seal and the removable cap;
   4. the malleable seal (a) is located between the removable cap and the piezoelectric element, (b) holds the piezoelectric element or piezoelectric element support/piezoelectric element assembly in place within the holder and (c) forms a seal around the piezoelectric element or around the piezoelectric element support that prevents gasses from entering from the exposed side of the piezoelectric element into the enclosed region defined by the piezoelectric element support and the piezoelectric element; and
   5. the electrical circuit means includes at least one point of contact spaced apart from the point of contact of the first electrode with the piezoelectric element.

2. The holder of claim 1, wherein a point of contact of the electrical circuit means with the periphery or exposed side of the piezoelectric element is the malleable seal.

3. The holder of claim 1, wherein the removable cap is threaded and screwed onto the body.

4. The holder of claim 1, wherein the removable cap is a halo that is affixed to the body via one or more screws or bolts.

5. The holder of claim 1 wherein the piezoelectric element rests against the piezoelectric element support without being affixed thereto, and is held into place against the piezoelectric support via the removable cap and the malleable seal.

6. The holder of claim 1 wherein the malleable seal is gold or a gold alloy containing at least 50% by weight gold.

7. The holder of claim 1 having a piezoelectric element mounted on the piezoelectric element support.

8. The holder of claim 1 further comprising means for introducing a purge gas into the enclosed region on the reverse side of the piezoelectric element, and a vent means for removing the purge gas from the enclosed region.

* * * * *